United States Patent
Gissmann et al.

(10) Patent No.: US 6,599,508 B1
(45) Date of Patent: *Jul. 29, 2003

(54) PAPILLOMA VIRUS-LIKE PARTICLES, FUSION PROTEINS AS WELL AS PROCESSES FOR THEIR PRODUCTION

(75) Inventors: Lutz Gissmann, Willowbrook, IL (US); Jian Zhou, Willowbrook, IL (US); Martin Muller, Chicago, IL (US); Jeanette Painstil, Westchester, IL (US)

(73) Assignee: Loyola University of Chicago, Chicago, IL (US)

( * ) Notice: Subject to any disclaimer, the term of this patent is extended or adjusted under 35 U.S.C. 154(b) by 15 days.

This patent is subject to a terminal disclaimer.

(21) Appl. No.: 09/949,404

(22) Filed: Sep. 6, 2001

Related U.S. Application Data

(62) Division of application No. 09/397,680, filed on Sep. 16, 1999, now Pat. No. 6,361,778, which is a division of application No. 08/817,335, filed as application No. PCT/EP95/03974 on Oct. 9, 1995, now Pat. No. 6,066,324.

(30) Foreign Application Priority Data

Oct. 7, 1994 (DE) .......................................... 44 35 907
Jul. 21, 1995 (DE) .......................................... 195 26 752

(51) Int. Cl.$^7$ .............................................. A61K 39/12
(52) U.S. Cl. .............................. 424/204.1; 424/205.1; 424/184.1; 424/186.1; 435/69.1; 435/69.3; 536/23.72

(58) Field of Search .......................... 424/204.1, 205.1, 424/184.1, 186.1, 199.1; 435/69.1, 69.3; 536/23.72

(56) References Cited

FOREIGN PATENT DOCUMENTS

| WO | WO 93/02184 | 2/1993 |
| WO | WO 93/20844 | 10/1993 |
| WO | WO 94/00152 | 1/1994 |

OTHER PUBLICATIONS

Jochmus et al, Archives of Medical Research, 1999, vol. 30, pp. 269–274.*
Michel et al, Virology, 2002, vol. 294, pp. 47–59.*
Altmann, et al., "Towards HPV Vaccination," in Minson A., Neil J., McCrae M. (eds): Viruses and Cancer, Cambridge University Press, pp. 71–80 (1994).
Wettstein, et al., "State of Viral DNA and Gene Expression in Benign VS. Malignant Tumors," in Pfister H. (ed): Papilloma viruses and Human Cancer, Boca Raton, 8:155–179 (1990).

* cited by examiner

Primary Examiner—Ali R. Salimi
(74) Attorney, Agent, or Firm—Marshall, Gerstein & Borun

(57) ABSTRACT

The invention relates to the recombinant production of proteins as well as VLPs which are suitable as a vaccine for therapeutic and prophylactic vaccination. The invention also relates to processes for the production and purification of recombinant papilloma virus proteins and fusion proteins.

12 Claims, No Drawings

PAPILLOMA VIRUS-LIKE PARTICLES, FUSION PROTEINS AS WELL AS PROCESSES FOR THEIR PRODUCTION

This application is a divisional of U.S. application Ser. No. 09/397,680 filed Sep. 16, 1999, now U.S. Pat. No. 6,361,778, which in turn is a divisional of U.S. application Ser. No. 08/817,335 filed on Oct. 2, 1997, now U.S. Pat. No. 6,066,324 issued May 23, 2000 which is a 371 of PCT/EP 95/03974 filed Oct. 9, 1995.

FIELD OF THE INVENTION

1. The invention relates to recombinantly produced papilloma virus-like particles, proteins, fusion proteins as well as processes for the formation and purification of these particles, proteins and fusion proteins.

BACKGROUND OF THE INVENTION

2. Infections with certain (high-risk) types of genital papilloma viruses in humans (HPV), e.g. HPV 16, 18 or 45 are held to be the main risk factor for the formation of malignant tumours of the anogenital tract. Of these, cervical carcinoma is by far the most frequently occurring. According to an estimate aby the WHO, about half a million new cases of this disease occur annually. Because of this frequent occurrence, the connection between HPV infection and cervical carcinoma has been the best investigated:

a) Precursor lesions of cervical carcinoma (cervical intraaepithelial neoplasia: CIN) are caused by papilloma virus infections.

b) The genomes of certain HPV types (e.g. 16, 18, 33, 35, 45) have been proven to occur in more than 95
   of tumour biopsies as well as in cell lines derived from them.

Depending on the geographic origin of the tumours, 5–70% of these contain HPV 16.

c) In all subsequently examined cases the ORFs E6 and E7 are transcribed (Wettstein et al., in Pfister H. (ed): Papilloma viruses and human cancer, pp. 155 to 179, Boca Raton, 1990).

d) The proteins E6 and E7 can be proven in all cervical-carcinoma cell-lines as well as in in vitro transformed human keratinocytes, and the majority of patients with cervical carcinoma have E6- or E7- specific antibodies.

e) The constitutive expression of the E6/E7 proteins is necessary to maintain the transformed condition of HPV-positive tumours.

f) The E6- and E7 genes of HPV 16 and HPV 18 are biologically active in the following experimental systems:
   Induction of cellular DNA synthesis in human cells;
   Transformation of human keratinocytes and other cells in culture;
   Tumour formation in transgenic mice.

3. Other HPV types (principally HPV 6 and 11) cause benign genital warts (condylomata acuminata) and are only extremely rarely associated with malignant tumours (low-risk types).

4. As a rule, genital papilloma viruses in humans are transmitted during intercourse and in most cases lead to persistent infection in the anogenital mucous membrane. This led to the conclusion that primary infections induce only an insufficient immune response, or that the virus has developed possibilities of avoiding the immune surveillance in the infected cells. On the other hand there are good indications suggesting that the immune system is involved during primary manifestation or during the malignant progression of papilloma virus infections. (For an overview see Altmann et al. (1994) in Minson A., Neil J., McCrae M. (eds): Viruses and cancer, Cambridge University Press, pp. 71 to 80).

a) In the case of animal papilloma viruses (rabbit papilloma virus and bovine papilloma virus), the clinical manifestation of primary infections can be avoided by vaccination with viral structural proteins or with wart extracts (autologous vaccines).

b) Rodents are protected by vaccination with HPV 16 E6- or E7-positive vaccinia recombinants or by synthetic peptides prior to tumour formation after inoculation of HPV 16- transformed autologous cells.

c) Regression of warts is often systemic and in the case of animal papilloma viruses can be induced by the transfer of lymphocytes of regressor animals.

d) In the case of immuno-suppressed patients (e.g. kidney transplantees or HIV-infectd persons), the incidence of genital warts, CIN and anogenital cancer is increased.

5. This led to the conclusion that papilloma virus-specific vaccinations aimed at preventing the primary infection and the occurrence of genital cancer should be possible.

6. 1. Avoidance of HPV infections is suitable by vaccination with the structural proteins L1 and L2 of the papilloma virus (prophylactic vaccination).

7. Because papilloma viruses cannot be propagated to adequate titres in cell cultures or other experimental systems, the viral proteins can only be produced by means of recombinant vectors. Recently, virus-like particles (VLPs) which, after expression of the viral structure proteins L1 and L2 (or L1 on its own), are formed in recombinant vaccinia or baculo virus, have been described. Purification of the VLPs can be achieved very simply by means of centrifugaton in CsCl- or sucrose gradients.

8. WO 93/02184 describes a method which provides papilloma virus-like particles (VLPs), which are used for diagnostic applications or as a vaccine against infections caused by the papilloma virus.

9. WO 94/00152 describes a recombinantly produced L1 main capsid protein which mimics the conformational neutralising epitope on human and animal papilloma virions. These recombinant proteins can be used as vaccines which protect against papilloma virus-infections.

10. 2. Treatment of cervical carcinoma or precursor lesions by immunotherapy assisted by early papilloma virus-proteins (principally E6 or E7) which are expressed in the persistently infected cells (therapeutic vaccination).

11. It is assumed that by this vaccination, cytotoxic T-cells are activated against persistently infected genital lesions. The target population are patients with HPV associated pre-malignant or malignant genital lesions.

12. Early HPV proteins are produced by expression in *E. coli* or eukaryotic vectors (e.g. baculo virus or yeast).
Purification is however rendered difficult by the low solubility and as a rule requires a combination of ion exchange chromatography, gel filtration and affinity chromatography.

13. PCT patent application WO 93/20844 discloses that the E7 protein of the papilloma virus from HPV or BPV is therapeutically effective in the regression (not however in the prevention) of papilloma virus-tumours in mammals. In addition, preferred antigenic proteins fragment sequences are described.

14. So far, however, no VLPs were described which are suitable both for prophylactic and therapeutic vaccination.

The last-mentioned processes have the disadvantage that, for example, early HPV proteins, because of their low solubility, can only be cleaned with difficulty.

15. A high particle production would be particularly desirable, in particular in view of a vaccine for prophylactic and therapeutic vaccination.

16. A disadvantage for the process described so far was that it was not possible to produce VLPs after expression of L1 in E. coli.

DESCRIPTION OF THE INVENTION

17. It is therefore the object of the present invention, to make available recombinantly produced proteins as well as VLPs which are suitable as a vaccine for prophylactic and therapeutic vaccination, as well as processes for the production of these proteins and VLPs. Equally, simple purification of the recombinant proteins obtained should be possible. Also production of VLPs after expression of L1 in E. coli should be possible.

18. The present invention accomplishes this task according to VLPs stated in the independent claims 1 and 12; the proteins stated in the independent claim 36; the fusion proteins stated in the independent claims 8 and 38; the processes stated in the claims 42 and 43; and the use according to claims 55 and 56. Further preferred embodiments, aspects and details of the invention are disclosed in the dependent claims of the description as well as in the preferred embodiments.

19. According to the present invention, VLPs are produced which consist of fusion proteins of late and early HPV proteins (or fragments thereof) (HVLP) and which can be used for prophylactic or therapeutic vaccination. Such a vaccine offers the following advantages when compared with conventional preparations:

a) In the case of prophylactic vaccination, HVLPs, through induction of L1/L2-specific antibodies not only prevent entry of the virus into the cell but they also eliminate already infected cells (through induction of cytotoxic T-cells) if an infection has taken place earlier or if the humoral immune response was in adequate.

b) In the case of therapeutic vaccination, HVLPs eliminate persistently infected cells (e.g. in patients with CIN or cervical carcinoma), and above all they prevent re-infection in female patients with CIN lesions.

c) Purification of the HVLPs is simple, in a similar way to purification of the VLPs without early HPV proteins.

20. According to the present invention, VLPs of the bovine papilloma virus (BPV) type 1 and the human papilloma viruses 11 and 16 after expression of L1 plus L2, or L1 on its own, can be produced in vaccinia or baculo virus. Experiments show that parts of the L1 protein can be deleted (amino acid sequence 311–351, 331–371, 391–431 of BPV 1; 306–315 of HPV 16), without the ability to form VLPs being lost. Such sections exist in the L1 proteins of all papilloma viruses so that the deleted section of L1 can be replaced by other proteins (of papilloma viruses or of other origin) and that in this way, hybrid virus-like particles can be produced. In the same way, parts of the papilloma virus protein L2 are deleted and replaced by other (early HPV or other) proteins, so that HVLPs can also be formed from the complete L1 protein plus an L2 fusion protein.

21. Fusion proteins comprising deleted L1 or L2 protein from different HPV types (principally HPV 6, 11, 16, 18, 33, 35, 45) and the respective early proteins E1, E2, E4, E5, E6, E7 (or parts thereof) are produced by expression in vaccinia recombinants which can be constructed in a very short time. The formation of VLPs, consisting either of a L1 fusion protein or of the complete L1 protein plus an L2 fusion protein, is monitored by electron microscopy, and the presence of the early HPV protein is tested by Western blot analysis by means of specific antisera. For large-scale production of HPLVs the expression of the proteins is carried out in viral or eukarytic systems, preferably in baculo virus or in yeast.

22. Respective experiments for producing fusion proteins can be carried out with proteins of other origin.

23. Essential for the present invention are recombinantly produced virus-like particles (VLPS) which are formed after expression of the viral structural proteins L1 and/or L2, whereby sections of the L1 and/or L2 protein are deleted, without the ability of forming VLPs being lost.

24. According to the present invention, the deleted section in the L1 protein of the bovine papilloma virus type 1 preferably concerns the amino acid sequences 311–351, 331–371, 391–431. In the case of L1 proteins of the human papilloma virus 16, it advantageously concerns the amino acid sequence 306–315.

25. In a preferred embodiment of the present invention the deleted section of L1 and/or L2 proteins are replaced by other proteins or protein fragments, whereby fusion proteins are obtained. The share of L1 or L2 proteins is advantageously approx. 50 to 99%, preferably approx. 60 to 90%, particularly preferred approx. 80%.

26. However, according to the present invention, even if this is not explicitly stated below, more than one section of the L1 and/or L2 protein should also be deleted and preferably be replaced by other proteins or protein fragments.

27. It is particularly preferred to replace the deleted section in the L1 or L2 protein by other proteins of papilloma viruses and/or proteins of other origin, whereby hybrid virus-like particles (HVLPs) can be produced.

28. It has been shown to be particularly favourable according to the present invention, if the formation of the VLPs is from an L1 fusion protein or, according to a further embodiment, from a complete L1 protein and a L2 fusion protein.

29. The fusion proteins, in particular for the formation of hybrid virus-like particles according to a further embodiment of the present invention, preferably consist of a deleted L1 and/or L2 protein of different HPV types (human papiloma virus), particularly preferred are HPV 6, 11, 16, 18, 33, 35 and 45, and other proteins or protein fragments. Preferably these other proteins or protein fragments concern respective early proteins or fragments thereof, such as for example the early proteins E1, E2, E4, E5, E6 and/or E7.

30. According to the process covered in the invention, the expression of the fusion proteins and proteins is carried out in viral or eukaryotic vectors; particularly preferred in baculo viruses or in yeasts.

31. According to a further embodiment of the process according to the invention, the fusion proteins are produced through expression in vaccinia recombinants.

32. According to the present invention, the application of the fusion proteins or the hybrid virus-like particles for the production of a prophylactic and therapeutic vaccine preferably takes place after adding further components.

33. Up to now, for the production of VLPs, such as for example of VLPs from HPV 16, the L1 (ORF) was expressed by means of eukaryotic vectors, such as for example baculo virus. Formation of the VLPs (assembly) takes place in the karyon of infected cells.

34. Essential to the present invention are therefore in particular recombinant papilloma virus-like particles which are formed after expression of the viral structural proteins L1 and/or L2, in which one or several sections of the L1 and/or L2 proteins are deleted, whereby the ability to form virus-like particles is increased in comparison to the native formation and/or in vitro production.

35. According to the present invention, at least one of the deleted sections in the L1 and/or L2 protein of a papilloma virus is a deletion, advantageously in the C-terminal amino acid sequence, preferably approximately 1 to 34 amino acids in length, preferably from 1 to 26 amino acids in length, in particular 26 amino acids in length.

36. Advantageously, after insertion of the C-terminal deletion into the L1 and/or L2 protein, the production of VLPs is increased many times, preferably at least 10 times, and in particular approx. 10 to 100 times.

37. In a preferred embodiment of the present invention, the deleted sections in the L1 and/or L2 protein, in particular of the bovine papilloma virus, concern 26 C-terminal amino acids. Particularly preferred is the C-terminal deletion, 26 amino acids in length, (Gly-Ala-Gly-Cys-Ser-Thr-Val-Arg-Lys-Arg-Arg-Ile-Ser-Gln-Lys-Thr-Ser-Ser-Lys-Pro-Ala-Lys-Lys-Lys-Lys-Lys) (SEQ ID NO:2) corresponding to the nucleotide positions 7016 to 7093 GGGGCAGGAT GTTCAACTGT GAGAAAACGA AGAATTAG CC AAAAAACTTC CAGTAAGCCT GCAAAAAAAA AAAAAAAA (SEQ ID NO:1) is inserted into the L1 ORF of the bovine papilloma virus type 1 (BPV 1). Advantageously, after inserting the C-terminal deletion into the L1 and/or L2 protein, the production of VLPs is increased at least ten times.

38. According to a further embodiment of the present invention, the deletion, of which there is at least one, in the L1 and/or L2 protein concerns a homologous amino acid sequence of the human papilloma virus 16 or of other papilloma viruses.

39. According to a further preferred embodiment, the deleted sections in the L1 and/or L2 protein concern 34 C-terminal amino acids of the human papilloma virus type 16 (HPV 16); preferably the amino acid sequence (Ala-Gly-Leu-Lys-Ala-Lys-Pro-Lys-Phe-Thr-Leu-Gly-Lys-Arg-Lys-Ala-Thr-Pro-Thr-Thr-Ser-Ser-Thr-Ser-Thr-Thr-Ala-Lys-Arg-Lys-Lys-Arg-Lys-Leu) (SEQ ID NO:4) corresponding to the nucleotide positions 7052 to 7153 GCAGGATTGA AGGCCAAACC AAAATTTACA TTAGGAAAAC GAAAAGCTAC ACCCACCACC TCATCTACCT CTACAACTGC TAAACGCAA AAACGTAAGC TG (SEQ ID NO:3), which is inserted into the L1 ORF of the HPV 16.

40. It is particularly preferred if the deletion of the L1 and/or L2 protein comprises the nuclear localisation signal (NLS). Particle production from the L1 proteins or the L1 proteins and L2 proteins takes places in particular in the cytoplasm. Preferably, the particles are secreted into the supernatant liquid; particularly preferred is a secretion of approx. 5 to 10% of the particles.

41. The expression of L1 proteins or L1 proteins and L2 proteins in E. coli takes place according to a further preferred embodiment. In this, at the C-terminal deletion in the L1 protein, in particular in addition 6 histidines are inserted. Advantageously the production of VLPs takes place after expression of L1 proteins or L1 and L2 proteins in E. coli.

42. According to the present invention, the further deleted sections in the L1 protein of the bovine papilloma virus type 1 preferably concern the amino acid sequences 311–351, 331–371, 391–431. Advantageously the L1 proteins of the human papilloma virus 16 concern the amino acid sequence 306–315.

43. In a preferred embodiment of the present invention, the further deleted section of L1 and/or L2 proteins is replaced by other proteins or protein fragments, whereby proteins are obtained which in this document are called fusion proteins. Advantageously, the content of L1 or L2 protein is approx. 50 to 99%, preferably approx. 60 to 90%, particularly preferred approx. 80%.

44. However, according to the present invention, even if this is not explicitly stated, more than one further section of the L1 and/or L2 protein should be deleted and preferably be replaced by other proteins or protein fragments.

45. It is particularly preferred if the deleted section of L1 or L2 protein is replaced by other proteins of papilloma viruses and/or proteins of other origin, whereby hybrid virus-like particles (HVLPs) can be produced.

46. It has been shown particularly advantageous according to the present invention, that the formation of the VLPs takes place from an L1 protein, an L1 fusion protein, an L1 protein and L2 protein, an L1 fusion protein and an L2 protein, an L1 protein, and an L2 fusion protein or an L1 fusion protein and an L2 fusion protein.

47. According to a further embodiment of the present invention, at least one of the deleted sections in the L1 and/or L2 protein of a papilloma virus concerns N-terminal amino acid sequences.

48. According to the present invention, in a further embodiment at least one of the deleted sections in the L1 protein and/or L2 protein of a papilloma virus concerns amino acid sequences in the middle section of the protein.

49. Also essential for the invention are proteins, in particular for the formation of hybrid papilloma virus-like particles, whereby one or several sections of the L1 and/or L2 protein are deleted. In particular, at least one of the deleted sequences in the L1 and/or L2 protein concerns the deletion of a C-terminal amino acid sequence.

50. The fusion proteins, in particular for the formation of hybrid papilloma virus-like particles according to a further embodiment of the present invention, advantageously consist of a deleted L1 and/or L2 protein of different papilloma viruses, specially preferred are HPV 6, 11, 16, 18, 31, 33, 35 and 45, and other proteins or protein fragments of papilloma viruses or of other origin. Preferably, these other proteins or protein fragments concern the respective early papilloma virus proteins or fragments concern the respective early papilloma virus proteins or fragments thereof, such as for example the early proteins E1, E2, E4, E5, E6, and/or E7.

51. According to the process covered in the invention, the expression of the proteins and/or fusion proteins and the production of papilloma virus-like particles is carried out in viral, eukaryotic or prokaryotic vectors, especially advantageous in vaccinia recombinants, in baculo viruses, in yeasts or in bacteria, in particular in E. coli.

52. Preferably particle production occurs in cytoplasm. In a particularly preferred manner, the particles are secreted into the supernatant liquid; it is particularly preferred if approx. 5 to 10% of the particles are secreted into the supernatant liquid.

53. In particular, according to the present invention, by inserting a C-terminal deletion, 25 amino acids in length, into the nucleotide positions 7016 to 7093 in the L1 ORF of the bovine papilloma virus type 1 (BPV 1), the production of VLPs is increased more than tenfold. Thus with the same quantity of L1 protein, as can be demonstrated for example in a Western blot, an increase in the particle number can be demonstrated in the electron microscope. Since deletion preferably comprises the nuclear localisation signal (NLS), the particle production takes place in the cytoplasm, a significant part of the particles is secreted into the supernatant liquid. This is particularly advantageous because it significantly facilitates purification.

54. Proteins, preferably with the mentioned deletion with additional 6 histidines (His L1 proteins), according to the present invention are expressed in *E. coli*. The proteins, in particular His L1 proteins, are preferably purified by way of Ni affinity chromatography, whereby according to an advantageous embodiment, at this point in time the proteins are present in a denaturation buffer, for example 6 M guanidine hydrochloride. Renaturation takes place for example in 150 mM NaCl, 1 mM $CaCl_2$, 0.01% Triton-X 100, 10 mM Hepes (N-2-hydroxyethyl piperazine-N'-2 ethane sulfonic acid), pH 7.4.

55. According to a preferred embodiment of the present invention, production (assembly) of the VLPs takes place after dialysis of the proteins, preferably after dialysis against 150 mM NaCl, 25 mM $Ca^{2+}$, 10% DMSO (dimethyl sulfoxide), 0.1% Triton-X 100, 10 mM tris [tris-(hydroxymethyl) aminomethane] acetic acid with a pH value of 5.0.

56. The deletion of sequence in the L1 protein of all papilloma viruses which prevent the premature assembly to the VLPs leads to a higher yield during VLP production.

57. As far as in these cases the L1 NLS is concerned, the assembly takes place in the cytoplasm. Consequently, according to the invention, purification of the VLPs is possible from the cytoplasm, instead of, as up to now, from the karyon. According to the invention, shorter deletions are also possible. According to the present invention, deletions of up to one amino acid and/or substitutions of up to one amino acid are carried out. In this it is advantageous that with short deletions or substitutions of up to one or only a few amino acids, the antigenic properties of the proteins and the LVPs formed thereof, are changed as little as possible when compared to the native antigenic properties of the proteins or VLPs.

58. The introduction of a C-terminal deletion or substitution in L1 and/or L2 fusion proteins, as carried out previously, also leads to an increase in the production of hybrid VLPs. In this, those VLPs should also be included which only contains L1 fusion proteins, as well as hybrid VLPs which contain an L1 or L2 fusion protein and a L2 or L1 protein.

59. For this, VLPs are produced which comprise fusion proteins of late and early HPV proteins (or fragments thereof) (HVLPs) and which can be used for prophylactic or therapeutic vaccination. Such a vaccine offers the following advantages when compared with conventional preparations:

a) In the case of prophylactic vaccination, HVLPs, through induction of L1/L2-specific antibodies not only prevent entry of the virus into the cell but they also eliminate already infected cells (through induction of cytotoxic T-cells) if an infection has taken place earlier or if the humoral immune response was inadequate.

b) In the case of therapeutic vaccination, HVLPs eliminate persistently infected cells (e.g. in patients with CIN or cervical carcinoma), and above all they prevent reinfection in female patients with CIN lesions.

c) Purification of the HVLPs is simple, in a similar way to purification of the VLPs without early HPV proteins.

60. VLPs of the bovine papilloma virus (BPV) type 1 and the human papilloma viruses 11 and 16 after expression of L1 plus L2, or of L1 on its own, can be produced in vaccinia or baculo virus. Experiments show that parts of the L1 protein can be deleted (amino acid sequences 311–351, 331–371, 391–431, of BPV 1; 306–315 of HPV 16), without the ability to form VLPs being lost. Such sections exist in the L1 proteins of all papilloma viruses so that the deleted section of L1 can be replaced by other proteins (of papilloma viruses or of other origin) and that in this way, hybrid virus-like particles can be produced. In the same way, parts of the papilloma virus protein L2 are deleted and replaced by other (early HPV or other) proteins, so that HVLPs can also be formed from the complete L1 protein plus an L2 fusion protein.

61. Fusion proteins comprising deleted L1 or L2 protein from different HPV types (mainly HPV 6, 11, 16, 18, 33, 35, 45) and the respective early proteins E1, E2, E4, E5, E6, E7 (or parts thereof) are produced by expression in vaccinia recombinants which can be constructed in a very short time. The formation of VLPs, consisting either of an L1 fusion protein or of the complete L1 protein plus an L2 fusion protein, is monitored by electron microscopy, and the presence of the early HPV protein is tested by Western blot analysis by means of specific antisera. For large-scale production of HPLVs the expression of the proteins in viral eukaryotic or prokaryotic systems, preferably in baculo virus, in yeast, or in *E. coli*, is carried out.

62. According to the present invention, the application of the fusion proteins or the hybrid virus-like particles for the production of a prophylactic and therapeutic vaccine preferably takes place after adding further components.

63. Respective experiments for producing fusion proteins can be carried out with proteins of other origin.

---

What is claimed is:

1. A vaccine comprising a papillomavirus virus-like particle (VLP) consisting of a truncated papillomavirus L1 protein, said truncated L1 protein consisting of an amino acid sequence having one or more carboxy terminal amino acid residues deleted from a full length L1 amino acid sequence, said papillomavirus L1 protein derived from a viral strain selected from the group consisting of BPV, HPV 6, HPV 11, HPV 16, HPV 18, HPV 33, HPV 35 and HPV 45, and a pharmaceutically acceptable carrier.

2. The vaccine of claim 1 wherein the papillomavirus L1 protein is derived from HPV 16.

3. The vaccine of claim 2 wherein said deletion comprises from 1 to 34 carboxy terminal amino acid residues, and wherein said deletion increases the ability of the L1 protein to form virus-like particles compared to native L1.

4. The vaccine of claim 2 wherein the truncated L1 protein consists of an amino acid sequence having 34 amino acid residues deleted from the carboxy terminus of the full length L1 amino acid sequence.

5. The vaccine of claim 2 wherein the truncated L1 protein consists of an amino acid sequence having 26 amino acid residues deleted from the carboxy terminus of the full length L1 amino acid sequence.

6. A vaccine comprising a papillomavirus virus-like particle (VLP) consisting of a truncated papillomavirus L1 protein and amino acid residues from a second protein, said truncated L1 protein consisting of an amino acid sequence having one or more carboxy terminal amino acid residues deleted from a full length L1 amino acid sequence, said papillomavirus L1 protein derived from a viral strain selected from the group consisting of BPV, HPV 6, REV 11, HPV 16, HPV 18, HPV 33, HPV 35 and HPV 45, said amino acid residues from the second protein replacing deleted amino acid residues in the truncated L1 protein, and a pharmaceutically acceptable carrier.

7. The vaccine of claim 6 wherein the papillomavirus L1 protein is derived from HPV 16.

8. The vaccine of claim 7 wherein said deletion comprises from 1 to 34 carboxy terminal amino acid residues, and wherein said deletion increases the ability of the L1 protein to form virus-like particles compared to native L1.

9. The vaccine of claim 7 wherein the truncated L1 protein consists of an amino acid sequence having 34 amino acid residues deleted from the carboxy terminus of the full length L1 amino acid sequence.

10. The vaccine of claim 7 wherein the truncated L1 protein consists of an amino acid sequence having 26 amino acid residues deleted from the carboxy terminus of the full length L1 amino acid sequence.

11. The vaccine according to any one of claim 6–10 wherein the amino acid residues derived from the second protein are all or part of an HPV early protein selected from the group consisting of E1, E2, E3, E4, E5, E6, and E7.

12. The vaccine of claim 11 wherein the early protein is E7.

* * * * *

UNITED STATES PATENT AND TRADEMARK OFFICE
CERTIFICATE OF CORRECTION

PATENT NO.    : 6,599,508 B1
DATED         : July 29, 2003
INVENTOR(S)   : Lutz Gissmann et al.

It is certified that error appears in the above-identified patent and that said Letters Patent is hereby corrected as shown below:

<u>Column 10,</u>
Line 42, please delete "REV 11" and insert -- HPV 11 --.

Signed and Sealed this

Thirtieth Day of September, 2003

JAMES E. ROGAN
*Director of the United States Patent and Trademark Office*

SEQUENCE LISTING

<160> NUMBER OF SEQ ID NOS: 4

<210> SEQ ID NO 1
<211> LENGTH: 78
<212> TYPE: DNA
<213> ORGANISM: Bovine papillomavirus

<400> SEQUENCE: 1

```
ggggcaggat gttcaactgt gagaaaacga agaattagcc aaaaaacttc cagtaagcct      60
gcaaaaaaaa aaaaaaa                                                      78
```

```
<210> SEQ ID NO 2
<211> LENGTH: 26
<212> TYPE: PRT
<213> ORGANISM: Bovine papillomavirus

<400> SEQUENCE: 2

Gly Ala Gly Cys Ser Thr Val Arg Lys Arg Arg Ile Ser Gln Lys Thr
1               5                   10                  15

Ser Ser Lys Pro Ala Lys Lys Lys Lys
            20                  25

<210> SEQ ID NO 3
<211> LENGTH: 89
<212> TYPE: DNA
<213> ORGANISM: Human papillomavirus type 16

<400> SEQUENCE: 3
gcaggattga aggccaaacc aaaatttaca ttaggaaaac gaaaagctac acccaccacc       60
tcatctacct ctacaactgc taaacgcaa                                        89

<210> SEQ ID NO 4
<211> LENGTH: 34
<212> TYPE: PRT
<213> ORGANISM: Human papillomavirus type 16

<400> SEQUENCE: 4

Ala Gly Leu Lys Ala Lys Pro Lys Phe Thr Leu Gly Lys Arg Lys Ala
1               5                   10                  15

Thr Pro Thr Thr Ser Ser Thr Ser Thr Thr Ala Lys Arg Lys Lys Arg
            20                  25                  30

Lys Leu
```